United States Patent [19]
Snell et al.

[11] Patent Number: 4,596,255
[45] Date of Patent: Jun. 24, 1986

[54] APPARATUS FOR INTERPRETING AND DISPLAYING CARDIAC EVENTS OF A HEART CONNECTED TO A CARDIAC PACING MEANS

[76] Inventors: Jeffery D. Snell, 17135 Bircher St., Granada Hills, Calif. 91344; Brian M. Mann, 12079 Beaufait, Northridge, Calif. 91326; Jason A. Sholder, 21037 Cantara St., Canoga Park, Calif. 91304

[21] Appl. No.: 701,795

[22] Filed: Feb. 15, 1985

Related U.S. Application Data

[63] Continuation of Ser. No. 440,149, Nov. 8, 1982, abandoned.

[51] Int. Cl.$^4$ .............................................. A61B 5/04
[52] U.S. Cl. .............................. 128/697; 128/419 PT
[58] Field of Search ................. 128/419 PT, 697, 710, 128/711, 712

[56] References Cited

U.S. PATENT DOCUMENTS

| | | |
|---|---|---|
| 3,782,363 | 1/1974 | Hochberg et al. ................... 128/697 |
| 4,098,267 | 7/1978 | Stein et al. ........................... 128/712 |
| 4,142,533 | 3/1979 | Brownlee et al. ............. 128/419 PT |
| 4,193,393 | 3/1980 | Schlager .............................. 128/702 |
| 4,281,664 | 8/1981 | Duggan ........................ 128/419 PT |

FOREIGN PATENT DOCUMENTS 639233 6/1950 United Kingdom ................ 128/712

OTHER PUBLICATIONS

Mancini et al., "IEEE Transactions on Biomedical Engineering", vol. 22, No. 4, Jul. 1975, pp. 281–286.

*Primary Examiner*—William E. Kamm
*Attorney, Agent, or Firm*—Robert R. Meads; Bryant R. Gold

[57] ABSTRACT

The present invention is an apparatus (1) for interpreting and displaying cardiac events of a heart connected to a cardiac pacing means (2) comprising a telemetry head (4), a first interpreting mean 6 with means connected to said telemetry head (4), a second interpreting means (12) with means connected to a plurality of ECG electrodes having paddles 8a at their digital end via electrical conduit (10), a control means (14) with means connected to said first and second interpreting means, (6) and (12) respectively, a multi-section memory means (16) with means connected to said control means (14), a D/A convertor (20) with means connected to said memory (16) a printing means (22) with means connected to said D/A convertor (20), logic means (24) with means connected to said memory means (16) and a display means (26) with means connected to said logic means (24).

8 Claims, 6 Drawing Figures

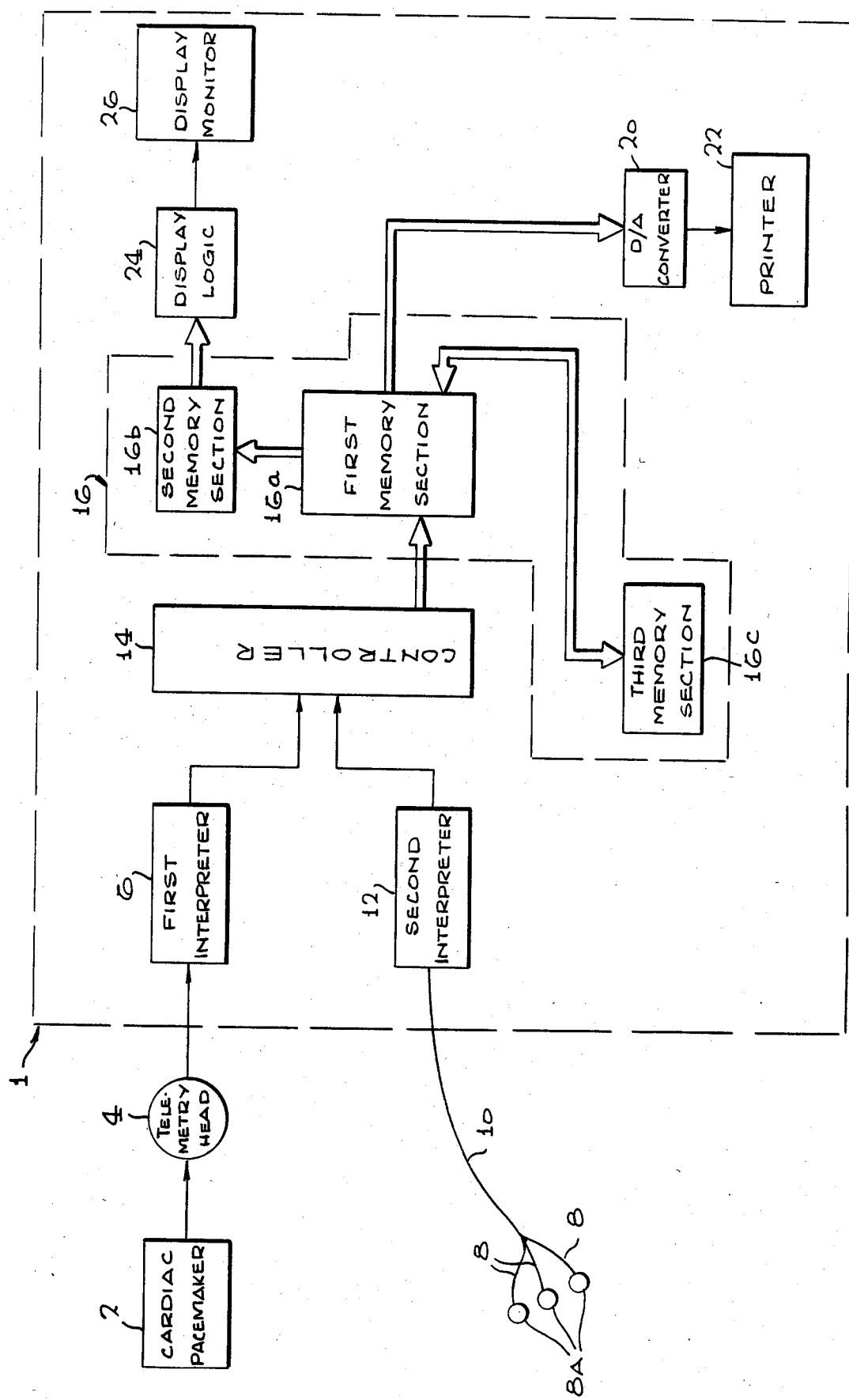

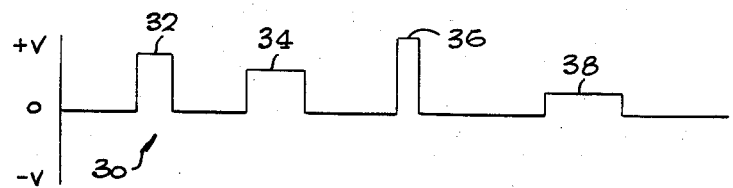
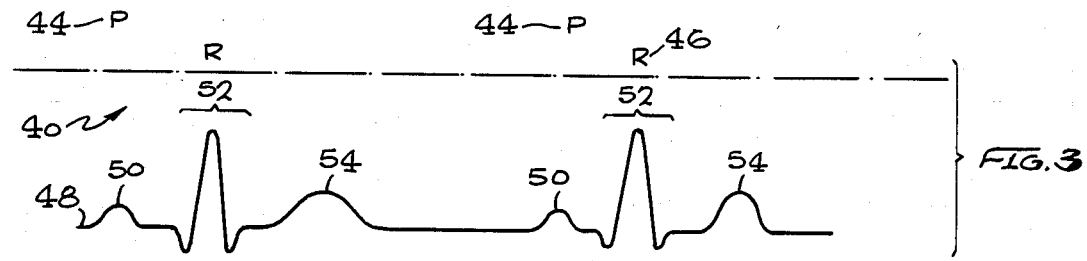
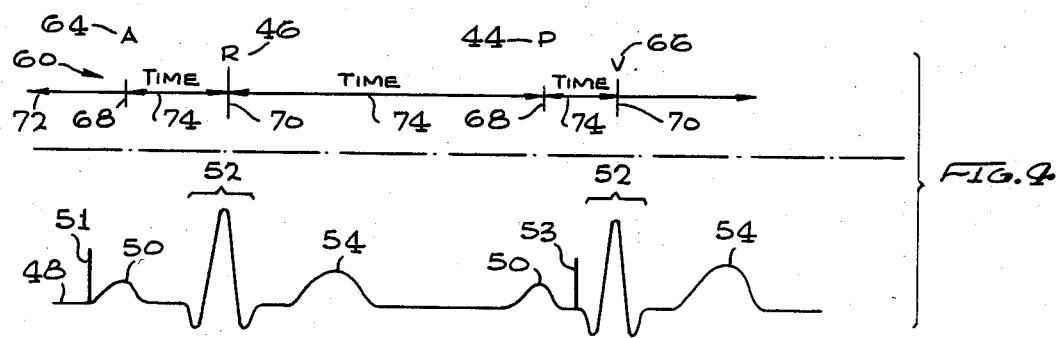
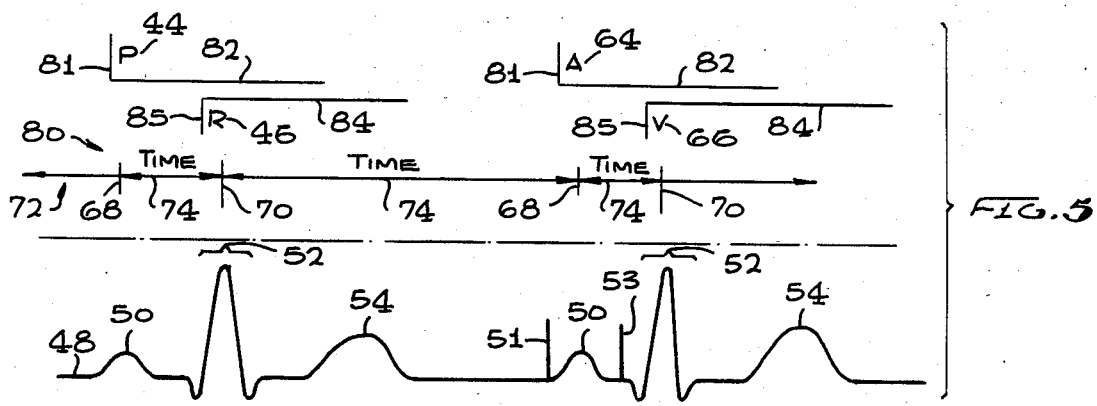
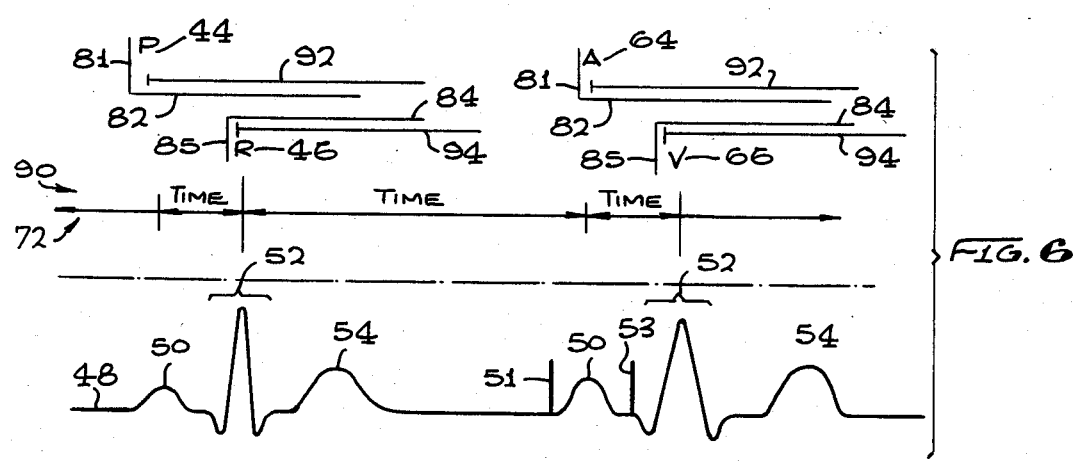

APPARATUS FOR INTERPRETING AND DISPLAYING CARDIAC EVENTS OF A HEART CONNECTED TO A CARDIAC PACING MEANS

This is a continuation of co-pending application Ser. No. 440,149 filed on Nov. 8, 1982 and now abandoned.

TECHNICAL FIELD

The technical field of the invention is the field of apparatuses which are capable of receiving telemetric signals from an implanted cardiac pacemaker and signals from ECG electrodes connected to the skin of an individual to provide a visual display representative of the cardiac events as seen by the cardiac pacemaker and a skin ECG wave pattern synchronized in real time. Further, the technical field of the invention is any field of diagnostic apparatuses which can be used for interpreting the activities of a heart connected to a cardiac pacing apparatus.

BACKGROUND ART

In the past, there has been significant breakthroughs in the development of cardiac pacemakers. Such cardiac pacemakers are ones which are programmable and can pace in a variety of pacing modes. The pacemakers can pace in VOO, VVI, VVT, AOO, AAI, AAT, DOO, DVI and DDD modes. Such new and innovative pacemakers come close to simulating the ultimate physiological pacing apparatus. However, there still does exist a great difficulty in determining how a particular implanted pacing apparatus is functioning at any given point in time.

A great majority of diagnostic tools used to evaluate the performance of a cardiac pacemaker have been subordinated to activity which was not seen in real time. Such evaluation was reduced to the production of ECG tapes created by connecting the individual having the implanted pacing apparatus to a series of electrodes so that the ECG tape could be made. After this tape was made, the physician or other technical person would then view the tape using calipers. This inspection would determine whether the proper pacing scheme was being accomplished for the individual having the implanted pacing apparatus (or pacemaker).

In most cases in the past, this evaluation did not take place in real time. It could be hours, days, or even weeks before a proper evaluation could be made as to whether proper pacing was taking place. There has not been any attempts to develop a diagnostic tool which could display a visual representation of the actual pacemaker activity and its associated ECG wave pattern in real time. The major problem in development of such a diagnostic apparatus was centered on the lack of the ability to provide visual representations of sequential cardiac events as seen by the pacing apparatus.

In the past, there has been futile attempts to provide outputs from the pacing apparatus as to mark cardiac events. The events that could not be effectively marked were outputs from the pacer to indicate an atrial or ventricular pulse to cause a depolarization of the cardiac chambers or when the pacing apparatus senses a natural P-wave or R-wave. There were no devices, which over a long period of time could actually provide information indicative of the complete sequence of cardiac events as seen by the pacer.

Coupled with the problems identified in the foregoing paragraphs, there has also been additional problems in determining whether the pacemaker was performing in a manner such that there were proper refractory periods following depolarization of the atrium or ventricle. In cases when the natural refractory period of the heart was not long enough to mask the next cardiac event such as a retrograde R-wave causing depolarization of the atrium, it was not desirable for such atrial depolarization to be detected by the pacing apparatus. In these situations it was desirable to get the pacemaker refractory periods at a length to insure that such retrograde depolarizations would not be detected. There was no device capable of determining the status of programmed refractory periods in respect to an ECG readout other than by doing extensive diagnostic interpretations of many ECG tapes.

In the past, there has also not been any quick and easy method by which a physician could display cardiac events in conjunction with an ECG wave pattern, such that both were synchronized in time. Such display of the cardiac events over the portion of the ECG wave pattern where it took place was not possible. Additionally, in situations where there were arrhythmias or other unnatural pacing problems, there were no devices capable of determining whether the events were truly what they appeared to be on the ECG wave pattern.

When this was the situation and the evaluation of the ECG tape was not in real time, the patient, if his pacing apparatus is not functioning properly, could possible die because there was not a quick evaluation in real time of what was going on. Therefore, because of the physician's inability to conduct such real time evaluations on a visual display, there could not be an effective evaluation of the proper or improper functioning of a cardiac pacing apparatus that was implanted.

These and others problems are solved by the apparatus of this invention.

DISCLOSURE OF INVENTION

The present invention is an apparatus which is capable of receiving at least two channels of information signals, process the channels of information signals and display on a display surface visual representations of the two channels of information signals.

The first channel of information signals are those which the apparatus receives telemetrically from an implanted heart pacing apparatus. These signals mark specific cardiac events as determined by (i.e., seen or generated) by the pacing apparatus. The cardiac events for which signals are telemetered from the pacing apparatus may be one or more of a sensed P-wave, a sensed R-wave, a ventricular pulse output by the pacing apparatus and a atrial pulse output by the pacing apparatus. The cardiac pacing apparatus outputs unique telemetric signals for the different cardiac events. The signals output by the cardiac pacing apparatus are encoded digital signals. Thus it is seen that the cardiac pacing apparatus sends telemetric signals as to events "determined" by it, i.e., events "caused" by the pacing apparatus and events "sensed" by the pacing apparatus. The word 'determined' is intended to cover both categories.

These signals are received by an antenna means, which in the case of the present invention is a telemetry head. The telemetry head transmits the signals to a first signal interpreting means which interprets the signals. The interpreted signals are then processed and sent in changed form as digital signals to a controller. The controller also receives signal inputs from a second signal interpreting means. The second signal interpreting means is connected to an electrical conduit which has ECG electrodes disposed at the end. Each of the electrodes have disposed at the distal end, paddles for attachment to the body of an individual. These electrodes take analog ECG readings of the individual having the heart pacing apparatus implanted therein. The analog signals from the ECG electrodes are transmitted through electrical conduit and received by the second signal interpreting means. The second signal interpreting means interprets and processes the signals and outputs a digital signal indicative of the signals to the controller.

The controller synchronizes, in real time, the two channels of information signals and outputs digital command signals to a memory. The memory receives the addressed signals from the controller and outputs memory signals to a display logic portion of the apparatus. The display logic portion then processes the memory signals through logic gates and provides an output of display command signals. The display command signals are received by the display monitor having display surface. The cardiac events are displayed over the ECG wave pattern on the display surface and they both are synchronized in the real time.

The apparatus is also able to receive and store within memory the refractory periods which were set for the implanted cardiac pacemaker. Each time that a cardiac event takes place, either a sensed P-wave, sensed R-wave, atrial pulse or ventricular pulse, the refractory period is displayed beneath the specific cardiac event in a linear fashion so that it will extend horizontally in real time in conjunction with the real time cardiac event and ECG wave pattern.

The cardiac pacing apparatus also outputs telemetric signals which mark the lengthening of the refractory periods of the pacing apparatus. These events are also processed by the apparatus and displayed on the display surface of the display monitor. The lengthened refractory periods of the pacemaker are displayed literally in a horizontal fashion as was described for the programmed refractory periods. However, such lengthened refractory periods are displayed adjacent to the programmed refractory period for the particular cardiac event.

Therefore, the present apparatus provides the diagnostic abilities not seen in any heretofore known apparatus. The present invention additionally has the ability to display the time periods between designated cardiac events. Such time periods could be between a P event and R event, R event and P event or any other combination of events that are desired by the physician or other technical person. These display time periods can be used for determining such things as AV delay, retrograde transmission time, and other specifics of the heart activity.

An object of the invention is to provide an apparatus which has the ability to receive telemetric signals from an implanted cardiac pacing apparatus and provides a display representative of the signals received which are indicative of different cardiac events.

Another object of the invention is to provide an apparatus which has the ability to receive telemetric signals from a cardiac pacing apparatus for signifying specific cardiac events and receiving signals from electrodes connected to the body of an individual, processing both sets of signals and providing a display of the signals which are synchronized in the real time that are indicative of both the cardiac events and the ECG wave pattern of an individual.

A further object of the invention is provide an apparatus which displays in real time representative symbols indicative of the sequential cardiac events as determined by an implanted cardiac pacing apparatus.

A still further object of the invention is to provide an apparatus which synchronizes an ECG wave pattern with sequential cardiac events such that the cardiac events are displayed over the point along the ECG wave pattern where they take place.

Another object of the invention is to provide along with the real time representation of the cardiac events the time period between designated events.

Another object of the invention is to provide a display of the specific sequential cardiac events in real time over the ECG wave pattern which is synchronized with the cardiac events, the time period between the cardiac events and the refractory periods when both the lengthened refractory period and programmed refractory period for pacing apparatus are displayed.

A further object of the invention is to provide an apparatus that can receive a plurality of telemetry signals from an implanted cardiac pacing apparatus where such telemetry signals are indicative of cardiac events which are capable of being displayed in real time or timed by the cardiac pacing apparatus.

These and other objects of the invention will be described in complete detail in the subsequent portions of this description.

BRIEF DESCRIPTION OF DRAWINGS

FIG. 1 shows a block diagram of the apparatus of the invention.

FIG. 2 shows representative encoded digital signal outputs the pacing apparatus for the different cardiac events which are telemetrically transmitted to the apparatus of invention.

FIG. 3 shows the primary embodiment of the display for the display surface of the apparatus of invention.

FIG. 4 shows a second embodiment of the display for the display surface of the apparatus of invention.

FIG. 5 shows the third embodiment of the display surface of the apparatus of invention. FIG. 6 shows a fourth embodiment of the display surface of the apparatus of invention.

BEST MODE FOR CARRYING OUT THE INVENTION

The present invention is an apparatus which interprets and displays cardiac events, as determined by an implanted cardiac pacemaker, and the ECG wave pattern in a synchronous manner on a display surface in real time.

Referring in FIG. 1, a block diagram of the apparatus of the invention is generally shown at 1. The telemetry Head 4 and ECG electrodes 8, with supporting electrical conduit 10, are part of the apparatus of invention but are detachably fixed to it.

The cardiac pacemaker 2 is a conventional type of programmable pacemaker with the added features of transmitting unique telemetric signals for different cardiac events as determined by the cardiac pacing apparatus. The cardiac events for which telemetric signals are transmitted are sensed P or R-waves, atrial or ventricular pulses generated by the cardiac pacemaker, and the end of the refractory period for the atrium or ventricle.

The unique telemetric signals transmitted by pacemaker 2 for indicating different cardiac events travel along line 3 extending from the cardiac pacemaker 2 to telemetry head 4. The signals are RF signals. However, even though the primary method of transmitting the signals is by use of telemetry, any other conventional means can be used. These RF signals transmitted by cardiac pacemaker 2 are encoded digital signals which are interpreted and processed will be desdribed subsequently.

Referring to FIG. 2, a representation of the wave forms for the unique signals transmitted by the cardiac pacemaker 2 in their decoded form is generally shown at 30. The square waves 32, 34, 36 and 38 all differ in some way. The pulses can vary in amplitude alone, pulse width alone or amplitude and pulse width together. In the preferred embodiment of the invention, each of the RF pulse wave forms are unique in both amplitude and pulse width for each cardiac event.

The first signal interpretor 6 receives the encoded RF pulses from telemetry head 4, interprets (or decodes) these signals initially and then processes the signals in accordance with the specific type of cardiac event the signal represents. the first interpretor 6 can be very simple because cardiac events take place sequentially, therefore, there will only be the need to interpret only one pulse (or signal) at any given point in time. The further processing of the signal after interpretation by first signal interpretor 6 consists mainly of preparing the signal as a first information signal input for controller 14.

The electrodes 8 are a plurality conventional ECG electrodes with paddles 8a attached to the distal end of each. The paddles 8a are attached to the skin of the individual in the normal manner for taking a skin ECG. When such attachment of paddles 8a take place, electrical signals (analog) are received from paddles 8a and transmitted to electrodes 8. These signals are transmitted through electrical conduit 10 to second signal interpretor 12. the second signal interpretor 12 receives the analog input, processes it and provides a digital output which is the second information signal input for controller 14.

Controller 14 receives the two informational signals. The first information signal is the digital output from first interpretor 6 and the second information signal is from the second signal interpretor 12. The controller has a variety of functions. One of the main functions is that it synchronizes the two input signals in time, and processes them in a parallel manner in controller 14. The controller accomplishes this by a switching method at about every 1 millisecond.

The Controller 14 also serves a communications sequencer and addressing means for the digital inputs.

To perform these functions, first the controller 14 takes the inputs, synchronizes them, and after such synchronization puts certain information on a data bus for memory 16 and provides certain command signals for addressing the data in the bus in memory 16. A majority of this data processing takes place automatically but there are some external commands that are input to controller 14 manually. These command signals which are externally controlled are the "Freeze" command and the "Expand" command which will be described subsequently.

Controller 14 provides the data and command outputs for three part memory 16. The first memory section, 16a, contains the software program information for controlling the apparatus. The second memory section, 16b, contains the information for controlling the hardware of the display monitor 16. The third memory section, 16c, is a bubble memory which contains additional memory for storing information which can be recalled at a later time. Memory section 16c is primarily used for recordation of data so that a physician or other technician can recall historical data on the patient when desired.

The connections between the memory sections 16a, 16b and 16c in the primary embodiment are as indicated in FIG. 1. The connection between the first section 16a and second section 16b is a unidirectional connection (from 16a to 16b). The connection 16a and 16c is bidirectional so that retrieval of stored information can be accomplished. This could also be accomplished using one large memory or a series of small memories and still be within the contemplation of the inventors.

First memory section 16a has an output to digital to analog (D/A) convertor 10. The D/A convertor 20 changes the digital output of section 16a to an analog output for driving printer 22. The use of this portion of the apparatus is primarily for printing out historical data on the patient stored in third memory section 16c.

The primary embodiment of the invention uses D/A convertor 20 and printer 22. However, the inventors also contemplate the use of a visual display surface which has logic means disposed between it and the memory which is responsive to the digital signal output by the memory. Therefore, there is no need for D/A convertor 20. The D/A convertor would only be necessary if the supplemental printer was attached to the display surface to produce a hard copy of the historical information retrieved from bubble memory 16c.

As previously stated, first memory section 16a provides a unidirectional output to second memory section 16b. The second memory section 16b contains in memory the information for controlling the display monitor 26. The signals from section 16a access section 16b causing a digital output from 16b to display logic portion 24.

The display logic portion 24 receives the output of memory section 16b and through a series of logic gates provides a digital output to display monitor 26. The output from memory section 16b to display logic 24 are the synchronized signals indicative of the signals from first and second signal interpretors 6 and 12. The synchronized signals, while being processed in the logic gates, retain their synchronized relationship when output from the display logic portion 24.

The output of display logic portion 24 drives display monitor 26 which has a display surface (or screen). The signals output by display logic portion 24 which drive display monitor 26 are processed by display monitor 26 is such a manner that each cardiac event will be represented by a unique character or symbol on the display surface. These cardiac events are also displayed sequentially in real time as they take place. The unique characters are displayed first at a first side of the surface and appear sequentially in time across the surface until they reach a second side of the display surface. When they reach the second side of the display surface they will switch back to the first side of the surface and repeat this procedure during the period telemetry signals are being received by the apparatus.

The second synchronized portion of signal driving display monitor 26, which is indicative of the ECG signals received and output by second interpretor 12, drives the monitor such that an ECG wave pattern is displayed on the display surface spaced away and beneath but synchronized with visual representations of the cardiac event being displayed above the ECG wave pattern.

The ECG wave pattern is a continuous wave pattern showing the P-wave, QRS complex and T-wave consistent with a normal ECG wave pattern. This wave pattern shows the actual ECG pattern for the person connected to paddles 8a. The wave pattern, like the cardiac event, begins at the first side on the surface but is displayed continuously as it takes place in time until it reaches a second side of the surface. When the wave pattern reaches the second side of the surface it switches back to the first side to continue the wave pattern. This will continue as long as the person is connected to paddles 8a of electrodes 8. The remaining figures, namely FIGS. 3 through 6, are the visual displays which are shown on the display surface (or screen) of display monitor 26.

Referring to FIG. 3, the basic visual representation of the telemetric signal received from cardiac pacing apparatus 2, indicative of cardiac events, and ECG signals, indicative of the skin ECG of an individual, are shown generally at 40. This is the representation that is shown on the display surface. The cardiac events are shown sequentially in time as 44 and 46 representing P-waves and R-waves, respectively. ECG pattern 48 is shown spaced away and below the representation for the cardiac events.

The cardiac events, at 44 and 46, and ECG pattern at 48 are synchronized in time. The wave displacements from the base line of the continuous ECG pattern which represent specific cardiac events have shown above them a unique cardiac event symbol. The unique cardiac events symbols are a "P" to represent a sensed P-wave, a "R" to represent a sensed R-wave, an "A" to represent an atrial pulse output by the cardiac pacing apparatus 2 to depolarize the atrium, or a "V" to represent a ventricular pulse output by cardiac pacing apparatus 2 to depolarize the ventricle. The P or A symbols are displayed in a position slightly higher than the R or V symbols because as in the heart the atrium is upper portion and ventricle the lower portion.

The physician or technician, as desired, can display either the sequential cardiac events 44 or 46 alone, ECG wave pattern 48 alone or both the cardiac events and ECG wave pattern simultaneously. The paragraphs hereafter will be directed to the simultaneous displaying of the synchronized visual outputs of the cardiac events and ECG wave pattern 48, however, singular representations are also contemplated by the inventors.

Referring again to FIG. 3, when the cardiac pacing apparatus 2 senses a P-wave, and a unique telemetric signal is output indicative of it, the representative symbol "P", 44, is displayed on the display surface. The continuous ECG wave pattern 48 will indicate P-wave 50 beneath the cardiac event symbol 44. As time progresses, the next sequential cardiac event, in a normal heart operating with pacing apparatus 2, is an R-wave. The representative symbol "R", 46 for the R-wave is displayed on the display surface. Beneath the symbol 46, the ECG wave pattern, that is synchronized with the cardiac event, displays QRS complex 52 which is representative of the R-wave. The ECG wave pattern 48 also will show T-wave 54 when sensed on the electrodes 8. However, the T-wave does not show up as a cardiac event. Although, if desired, there could be a representation of a T-wave on cardiac events line 48, the inventors did not want to show it because it is not one of the major depolarizations of one of the cardiac chambers and it is usually masked by the refractory periods of the chambers. There are no remaining cardiac events or the ECG wave forms displacements along 48 for the remainder of the heart cycle. After the cycle is completed, the foregoing is repeated, the cardiac events and the ECG wave pattern are displayed. This will continue to be repeated unless there happens not to be a natural depolarization of the ventricle or the atrium associated with premature activity.

When there is not a natural depolarization of the atrium or ventricle the pacing apparatus 2, will put out an electrical pulse to depolarize the chamber tissue that did not naturally depolarize. When this takes place, the representation symbol "A" (64 of FIG. 4) is displayed on the display surface. If a ventricular pulse is put out by the cardiac pacing apparatus 2, the representation symbol "V" (66 of FIG. 4) is displayed on the display screen. The symbols "A" and "V" are displayed over P-wave 50 and QRS complex 52 of the ECG wave pattern 48 because it is the "A" or "V" pulses that cause the depolarization of the respective chambers and cause the ECG wave deflection 50 and 52. Additionally, when the A or V pulses are output to cause depolarization, the electrodes 8 will be responsible to the output and a spikes 51 and 53 will be displayed on the display surface which are indicative of such output pulse.

In situations when the patient is experiencing a tachycardia of the atrium or ventricle, the actual sequence of depolarization will be shown on both the cardiac events line 42 and the ECG wave pattern 48. The method of using the displayed information to break such tachycardias will subsequently be described. However, whatever type of tachycardia takes place, there will be representative symbols for the cardiac events and the ECG pattern 48.

Referring to FIG. 4, a second embodiment of the visual display is shown generally at 60. As in FIG. 3, the cardiac events are displayed on the cardiac events line 42 and the ECG wave pattern is displayed at 48. The cardiac events line 42 show the representation symbols "A", 64, and "V", 66, for an atrial or ventricular pulse put out by the pacing apparatus 2, respectively. This secondary embodiment of the display has added thereto vertical indicators 68 and 70 to indicate the specific point of depolarization of the atrium or ventricle caused by a natural P-wave or atrial pulse from pacing apparatus 2; or natural R-wave or ventricular pulse from the pacing apparatus 2, respectively. In this embodiment, the indicators 68 and 70 are of different lengths, so at a glance it can be determined whether the cardiac event along the ECG wave pattern is from the group "P" or "A"; or the group "R" or "V".

Additionally, the apparatus has the ability to display the elapsed time between any two cardiac events. Therefore, the time intervals shown as "Time" at 74 will be displayed on the display surface in the indicated positions as numerals representing the length of the time interval. Although the time period 74, as shown only for those between consecutive events, there can be time periods displayed between any two events whether consecutive or not.

Referring to FIG. 5, a third embodiment of the display is shown generally at 80. This embodiment displays what was displayed in the embodiments of FIGS. 3 and 4 with the addition of horizontal indicators 82 and 84.

The horizontal indicators 82 and 84, in real time, indicate the programmed refractory periods of the atrium and ventricle as set in pacing apparatus 2. The horizontal indicator extends from the cardiac event to the end of the respective refractory period. The atrial programmed refractory period has and section 81 which extend upward from horizontal line 82. The ventricular programmed refractory period has end section 85 which extends down from horizontal line 84. This proves to be helpful information in determining whether the pacing apparatus 2 has been programmed with the proper refractory period. If the T-wave is not totally enclosed in the refractory period of the "P" or "A" it could cause another depolarization of the atrium. Therefore by viewing the display, it will indicate if the refractory period is too short for the characteristics of a particular heart.

Referring to FIG. 6, a fourth embodiment of the display is shown generally at 90. This embodiment has all of the features of the foregoing three embodiments with the added features of horizontal indicators 92 and 94, which indicate the actual refractory period of the pacemaker. The actual and programmed refractory periods of the pacemaker are the same except in cases when there is noise on the P or R sensing channels of the pacing apparatus 2. In such cases there is a lengthening of the programmed refractory period and the actual and programmed refractory periods are different. In such cases, the lengthened period will be displayed as 92 or 94.

In situations in which a patient has continued problems with tachycardias, the apparatus of the invention can be used to determine when the pulse should be delivered to break the tachycardia. The apparatus displays the period of time it takes to cause a depolarization in the atrium after a depolarization in the ventricle. This time period is the retrograde transmission time. The displayed time period will give the retrograde V-A delay. From this a physician can determine how to make the proper settings for the anti-tachycardia modes of the pacing apparatus 2 to break and prevent tachycardias. Likewise, in situations in which there is a tachycardia in the antegrade direction, the point of breaking the tachycardia can be determined by determining the A-V delay and when the best time to input a pulse to get ventricular capture.

The apparatus has means, which when activated will cause the current display to be "frozen" and "expanded" for high resolution of a particular visual display. This can also be done for information retrieved from bubble memory 16c. This frozen and expanded display can then be printed out on the printer 22.

Although the timed or cardiac events for which representative symbols or timing lines are displayed were for sensed P or R-waves, atrial or ventricular pulses output by the pacing apparatus, and programmed or lengthened refractory periods, there are other timed events or cardiac events which can be displayed on the display surface as long as telemetric signal marking the cardiac event or timed events an output by the pacing apparatus. Additionally, even though the preceding paragraphs state that the display surface displays cardiac events and an ECG wave pattern, there is also the ability of the apparatus to display other visual forms such as a ladder diagram or other similar figures. These figures will also be synchronized in real time with the figures represented on the display surface.

The terms and expressions which are employed here are used as terms of description and not of limitation and there is no intention, in the use of such terms and expressions, of excluding equivalents of the features shown, and described, or portions thereof, it being recognized that various modifications are possible in the scope of the invention as claimed.

We claim:

1. An apparatus for displaying cardiac events of a heart connected to an implanted cardiac pacemaker of a patient, said aparatus comprising:
    telemetry head means for receiving, in a first information channel, telemetered information from said implanted pacemaker;
    skin electrode means for receiving, in a second information channel, ECG information sensed at the skin of said patient, said ECG information being separate and distinct from the telemetered information received by said telemetry head means;
    controller means coupled to both said first and second information channels for synchronizing time the telemetered information received over the first information channel and the ECG information received over the second information channel, and for processing the information received over the first and second information channels in parallel while maintaining the synchronization therebetween, said controller means generating digital command signals representative of the information received over these first and second information channels and the synchronization therebetween;
    memory means for storing said digital command signals; and
    display means responsive to said digital command signals stored in said memory means for simultaneously displaying a synchronized representation of the telemetered and ECG information received over the first and second information channels.

2. The apparatus of claim 1 wherein said display means includes a display monitor having a display surface on which the telemetered information from the first information channel, and the ECG information, from the second information channel, are simultaneously displayed one above the other on the same time base.

3. The apparatus of claim 2 wherein said second information channel includes second interpreter means for digitizing the ECG information received by the skin electrode means.

4. The apparatus of claim 2 wherein said display means further includes a printer for printing the synchronized telemetered data stored in said memory means.

5. The apparatus of claim 2 wherein the telemetered information from said implanted pacemaker comprises RF encoded signals, the information included in these RF encoded signals including the occurrence of specified cardiac and pacemaker events as determined by said implanted pacemaker, such as an atrial contraction (P), a ventricular contraction (R), the generation of an atrial stimulation pulse (A), and the generation of a ventricular stimulation pule (V), and wherein said telemetry head means includes means for receiving said RF encoded signals and converting them to encoded digital signals, and further wherein said first information channel includes first interpreter means for initially decoding said encoded digital signals prior to presenting said signals to said controller means.

6. The apparatus of claim 5 wherein said display means includes means for displaying on said display surface the occurrence of said specified cardiac and pacemaker events as a distinguishing letter, such as a "P", "R", "A", or "V", said distinguishing letter being simultaneously displayed on the display surface in synchrony with the displayed ECG information received over the second information channel.

7. The apparatus of claim 6 wherein said means for displaying further includes means for displaying on said display surface, a horizontal time line with vertical line markers placed thereon, each vertical line marker having one of said distinguishing letters displayed therewith, and further including means for determining and displaying a numeric number on said display surface representing the time difference between adjcent vertical line markers as determined relative to the time base used by said display means.

8. The apparatus of claim 6 wherein said telemetered information received from said implanted pacemaker over said first information channel further includes refractory time periods associated with the operation of said implanted pacemaker, and wherein said display means includes means for displaying said refractory time periods as a horizontal line that is simultaneously displayed in synchrony with the ECG information received over the second information channel, the beginning, length, and ending of the horizontal line, as measured with respect to the time base, representing the beginning, length, and ending, respectively, of the refractory time period that is displayed.

* * * * *